(12) United States Patent
Boyle et al.

(10) Patent No.: US 6,679,902 B1
(45) Date of Patent: Jan. 20, 2004

(54) REDUCED PROFILE DELIVERY SHEATH FOR USE IN INTERVENTIONAL PROCEDURES

(75) Inventors: William J. Boyle, Fallbrook, CA (US); Andy E. Denison, Temecula, CA (US); Benjamin C. Huter, Murrieta, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 181 days.

(21) Appl. No.: 09/619,001

(22) Filed: Jul. 19, 2000

(51) Int. Cl.[7] .............................................. A61M 29/00
(52) U.S. Cl. ...................................................... 606/200
(58) Field of Search ......................... 604/264, 104–109, 604/103.1, 523, 529, 532, 536; 606/200

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,160,342 A | 11/1992 | Reger et al. |
| 5,192,286 A | 3/1993 | Phan et al. |

(List continued on next page.)

FOREIGN PATENT DOCUMENTS

| | | | |
|---|---|---|---|
| EP | 0 472 334 A1 | 2/1992 | |
| FR | 2 580 504 A1 | * 10/1986 | ................. 606/200 |
| GB | 2020557 | 11/1979 | |
| WO | WO92/03097 | 3/1992 | |
| WO | WO96/01591 | 1/1996 | |
| WO | WO97/17100 | 5/1997 | |
| WO | WO98/02084 | 1/1998 | |
| WO | WO98/33443 | 8/1998 | |
| WO | WO99/23976 | 5/1999 | |

*Primary Examiner*—Thomas Denion
*Assistant Examiner*—Thai-Ba Trieu
(74) *Attorney, Agent, or Firm*—Fulwider Patton Lee & Utecht, LLP (57) ABSTRACT

A delivery sheath is provided for deploying a self-expanding intravascular filter. The sheath includes a stiff proximal portion which provides for good pushability and trackability through tortuous vessels and a soft, flexible, low profile, radiopaque distal tip for holding and delivering a deployable filter. The soft distal tip minimizes the formation of embolic particles that may be produced by contact between the sheath and an arterial lesion. The distal tip may be molded from a polymer containing radiopaque particles held in suspension and thereby provides for good visualization under fluroscopy.

28 Claims, 3 Drawing Sheets

U.S. PATENT DOCUMENTS

| | | | |
|---|---|---|---|
| 5,324,304 A | * | 6/1994 | Rasmussen .................. 606/200 |
| 5,329,942 A | | 7/1994 | Gunther et al. |
| 5,330,482 A | | 7/1994 | Gibbs et al. |
| 5,350,398 A | | 9/1994 | Pavcnik et al. |
| 5,370,657 A | | 12/1994 | Irie |
| 5,383,887 A | | 1/1995 | Nadal |
| 5,421,832 A | | 6/1995 | Lefebvre |
| 5,449,372 A | * | 9/1995 | Schmaltz et al. ............ 606/198 |
| 5,490,859 A | | 2/1996 | Mische et al. |
| 5,496,277 A | | 3/1996 | Termin et al. |
| 5,496,330 A | | 3/1996 | Bates et al. |
| 5,501,694 A | | 3/1996 | Ressemann et al. |
| 5,549,626 A | | 8/1996 | Miller et al. |
| 5,601,595 A | | 2/1997 | Smith |
| 5,626,605 A | | 5/1997 | Irie et al. |
| 5,634,942 A | | 6/1997 | Chevillon et al. |
| 5,649,953 A | | 7/1997 | Lefebvre |
| 5,662,671 A | | 9/1997 | Barbut et al. |
| 5,669,933 A | | 9/1997 | Simon et al. |
| 5,681,347 A | * | 10/1997 | Cathcart et al. ............ 606/200 |
| 5,695,518 A | | 12/1997 | Laerum |
| 5,695,519 A | * | 12/1997 | Summers et al. ........... 606/200 |
| 5,700,252 A | * | 12/1997 | Klingenstein ............... 604/280 |
| 5,720,764 A | | 2/1998 | Naderlinger |
| 5,725,550 A | | 3/1998 | Nadal |
| 5,746,767 A | | 5/1998 | Smith |
| 5,755,708 A | * | 5/1998 | Segal ......................... 604/109 |
| 5,755,790 A | | 5/1998 | Chevillon et al. |
| 5,766,203 A | * | 6/1998 | Imran et al. ................. 606/200 |
| 5,769,816 A | | 6/1998 | Barbut et al. |
| 5,772,674 A | | 6/1998 | Nakhjavan |
| 5,779,716 A | | 7/1998 | Cano et al. |
| 5,792,145 A | | 8/1998 | Bates et al. |
| 5,792,156 A | | 8/1998 | Perouse |
| 5,792,157 A | | 8/1998 | Mische et al. |
| 5,795,322 A | | 8/1998 | Boudewijn |
| 5,800,457 A | | 9/1998 | Gelbfish |
| 5,800,525 A | | 9/1998 | Bachinski et al. |
| 5,810,874 A | | 9/1998 | Lefebvre |
| 5,814,064 A | | 9/1998 | Daniel et al. |
| 5,827,324 A | | 10/1998 | Cassell et al. |
| 5,833,650 A | | 11/1998 | Imran |
| 5,836,868 A | | 11/1998 | Ressemann et al. |
| 5,846,251 A | | 12/1998 | Hart |
| 5,846,260 A | | 12/1998 | Maahs |
| 5,848,964 A | | 12/1998 | Samuels |
| 5,868,708 A | | 2/1999 | Hart et al. |
| 5,876,367 A | | 3/1999 | Kaganov et al. |
| 5,897,567 A | | 4/1999 | Ressemann et al. |
| 5,910,154 A | | 6/1999 | Tsugita et al. |
| 5,911,734 A | | 6/1999 | Tsugita et al. |
| 5,941,896 A | | 8/1999 | Kerr |
| 5,968,071 A | | 10/1999 | Chevillon et al. |
| 5,976,172 A | | 11/1999 | Homsma et al. |
| 5,980,555 A | | 11/1999 | Barbut et al. |
| 5,989,281 A | | 11/1999 | Barbut et al. |
| 6,001,118 A | | 12/1999 | Daniel et al. |
| 6,013,093 A | | 1/2000 | Nott et al. |
| 6,059,814 A | * | 5/2000 | Ladd ......................... 606/200 |
| 6,152,946 A | | 11/2000 | Broome et al. |
| 6,156,006 A | * | 12/2000 | Brosens et al. ............. 604/104 |
| 6,171,327 B1 | | 1/2001 | Daniel et al. |
| 6,179,859 B1 | | 1/2001 | Bates et al. |
| 6,210,396 B1 | * | 4/2001 | MacDonald et al. ...... 604/103.1 |
| 6,264,671 B1 | * | 7/2001 | Stack et al. ................. 606/191 |
| 6,331,184 B1 | * | 12/2001 | Abrams ...................... 606/200 |
| 6,361,546 B1 | * | 3/2002 | Khosravi .................... 606/200 |
| 6,383,206 B1 | * | 5/2002 | Gillick et al. ............... 606/200 |
| 6,485,501 B1 | * | 11/2002 | Green ........................ 606/200 |
| 6,511,496 B1 | * | 1/2003 | Huter et al. ................. 606/200 |
| 6,511,503 B1 | * | 1/2003 | Burkett et al. .............. 606/200 |

* cited by examiner

REDUCED PROFILE DELIVERY SHEATH FOR USE IN INTERVENTIONAL PROCEDURES

BACKGROUND OF THE INVENTION

The present invention relates generally to the field of percutaneous transluminal treatment of stenosed or narrowed arteries in the human vascular system. More specifically, the invention is directed to a sheath for delivering intravascular filters for use in capturing embolic debris across tight lesions.

Arteries can become stenotic in a number of ways. Often, a stenosis or lesion forms due to an accumulation of atherosclerotic plaque on the walls of a blood vessel. Atherosclerotic plaque is typically a hard calcified substance, particles of which may dislodge during interventional procedures and flow freely in the circulatory system. A stenosis also may form from an accumulation of thrombus material which is typically softer than atherosclerotic plaque, but can nonetheless cause restricted blood flow in the lumen of a vessel. Like atherosclerotic plaque, thrombus material may sometimes dislodge during interventional procedures. Free flowing particulates, whether composed of plaque or thrombus material, are commonly referred to as emboli. Such free flowing emboli are dangerous since they may become lodged in small blood vessels and occlude or partially occlude the vessels.

Various approaches have been developed to treat a stenotic lesion in the vasculature. One of the most common is balloon angioplasty. Balloon angioplasty is directed towards relieving the constriction in the artery by radially expanding the stenosis to increase the diameter of the artery wall at the region of the stenosis. Another common procedure used to treat a stenotic lesion is atherectomy. In an atherectomy procedure, the stenosis is removed from the artery by the action of a cutting blade.

In a typical balloon angioplasty procedure, a guiding catheter is percutaneously introduced into the cardiovascular system of a patient through the femoral artery by means of a conventional Seldinger technique and advanced within a patient's vascular system until the distal end of the guiding catheter is positioned at a point proximal to the lesion site. A guide wire and a dilatation catheter having a balloon on the distal end are introduced through the guiding catheter with the guide wire sliding within the dilatation catheter. The guide wire is first advanced out of the guiding catheter into the patient's vasculature and is directed across the arterial lesion. The dilatation catheter is subsequently advanced over the previously advanced guide wire until the dilatation balloon is properly positioned across the lesion. Once in position, the expandable balloon is inflated to a predetermined size with a radiopaque liquid at a relatively high pressure to radially compress the atherosclerotic plaque of the lesion against the inside of the artery wall, thereby dilating the lumen of the artery. The balloon is then deflated to a small profile so that the dilatation catheter may be withdrawn from the patient's vasculature and blood flow resumed through the dilated artery. As should be appreciated by those skilled in the art, while the above-described procedure is typical, it is not the only method used in angioplasty.

The procedure for atherectomy is similar to that of balloon angioplasty in that a guiding catheter is introduced into the patient's vasculature through a conventional Seldinger technique and a guide wire is typically advanced through the guiding catheter and across an arterial lesion to a point distal of the lesion. However, rather than expanding the lesion and artery with a balloon as in angioplasty, in atherectomy, a specialized catheter containing rotating cutting blades is used to mechanically cut or abrade the stenosis from the wall of the artery.

With either of the above procedures, the treated artery wall suffers a degree of trauma and in a small percentage of cases may abruptly collapse or may slowly narrow over a period of time. To prevent either of these conditions, the treatment procedure may be supplemented by implanting within the arterial lumen a prosthetic device known as a stent. A stent is a small tubular metallic structure which is fitted over a catheter balloon and expanded at the lesion site. Stents serve to hold open a weakened blood vessel and help to prevent the blood vessel from collapsing or narrowing over time.

Balloon angioplasty, atherectomy, and stenting procedures have proven successful and are widely used in the treatment of stenosis of the coronary arteries and have, for many patients, rendered unnecessary invasive bypass surgery. However, all of the above procedures may create embolic particles which in certain critical arteries, such as the carotid arteries, may pose a significant risk of ischemic stroke. For this reason, these beneficial techniques have not been widely used in treating stenosis of the carotid arteries, leaving invasive bypass surgery as the primary treatment of choice.

Embolic particles may be created during balloon angioplasty because stenoses are often formed from hard calcified plaque which tends to crack when subjected to radial expansion of the inflatable balloon. Upon cracking, emboli may be released into a patient's bloodstream. Emboli may also be formed during a stenting procedure since the metal struts of the stent may cut into the stenosis and shear off plaque or thrombus material. During an atherectomy procedure, a constant stream of particles is cut from the stenosis. Typically, a suction catheter is used to capture these particles before the particles flow downstream in the vessel. However, it is often necessary to pull a high vacuum in order to remove all debris created by the cutting process. In some circumstances, it is not possible to pull a high enough vacuum to remove all debris without causing radial collapse of the weakened artery. Thus, some particles may not be drawn into the suction catheter and may flow downstream as emboli, where the particles may become lodged in small diameter blood vessels.

Numerous embolic filters or traps have been proposed, to capture embolic particles flowing distal of a lesion. The majority of these devices use some form of woven mesh basket. Some of these devices are self-expanding and are intended to be attached to a guide wire and delivered by a catheter or delivery sheath. Once the filter is in position in the vasculature, the sheath is removed from the collapsed filter to allow the filter to self-deploy to an expanded position within an artery. A typical example of the wire mesh basket type of intravascular filter is described in U.S. Pat. No. 4,873,978, entitled "Device and Method for Emboli Retrieval" issued to Ginsburg. Ginsburg discloses a removable vascular filter permanently attached to a guide wire for deployment from a catheter. The filter is comprised of an expandable wire mesh basket employing diamond shaped cells. Upon deployment, the filter expands to contact the walls of the lumen, thereby obstructing the vessel and straining blood flowing through the lumen.

One problem common to most types of intravascular filters is the process of delivering the filter to a point distal of the lesion without creating embolic particles prior to the filter's deployment. In delivering an intravascular filter, typically, a guiding catheter will have been previously advanced through the patient's vasculature to a point proximal of the arterial lesion. Subsequently, the filter along, with a delivery sheath which covers the collapsed filter, is advanced through the guiding catheter and across the arterial lesion. Then the sheath may be retracted to deploy the filter. Since arterial lesions tend to be formed of friable material, sufficient abrasion of the lesion caused by the delivery sheath while crossing the lesion or by any subsequent manipulation process required to deploy the filter may create embolic particles.

What is needed therefore is a delivery sheath with a sufficiently low profile that it may cross a lesion without causing any significant abrasion, which may lead to the creation of embolic particles. In addition, the sheath should have a soft and flexible distal tip to reduce trauma to the lesion in the event of contact during crossing and to reduce possible abrasion during deployment of the filter. Further, the filter should include features that allow for rapid deployment of the filter with a minimum of relative motion between the delivery sheath and the guide wire. The present invention meets these and other needs.

SUMMARY OF THE INVENTION

The present invention provides a delivery sheath for deploying collapsible intravascular filters. The delivery sheath includes a stiff proximal portion to help advance the sheath through a guiding catheter, and along a guide wire, and a soft distal tip for holding and delivering a deployable filter to a location distal of an arterial lesion. The proximal portion is produced from a material having relatively high stiffness, thereby giving the proximal portion high column strength which results in good pushability of the delivery sheath through tortuous vessels. The distal tip of the sheath is made from a softer, more pliable material than that of the proximal portion. The distal tip has a relatively low stiffness which minimizes trauma to the vessel caused by contact between the vessel and the distal tip. In addition, the distal tip is necked down from the proximal portion to form a reduced crossing profile. The reduced profile decreases the likelihood that the distal tip will contact an arterial lesion, while crossing the lesion, and consequently reduces the possibility that plaque will be abraded or sheared from the surface of the lesion.

In order to aid a vascular surgeon in placing the sheath under fluoroscopy or similar x-ray visualization procedures, the distal tip may be made radiopaque by molding the tip from a polymer material containing radiopaque particles, such as bismuth particles, held in suspension in the polymer. Alternatively, the distal tip may be equipped with radiopaque markers. The distal tip may be co-molded with the proximal portion to form a single unitary delivery sheath or the distal portion may be formed as a separate component which is attached to the proximal portion of the sheath by adhesives, ultrasonic welding, or other suitable bonding methods.

Abrasion between the sheath and the lesion during sheath introduction and filter deployement may be minimized by reducing the relative motion between the distal tip and the guide wire. This may be accomplished by partially loading the filter device within the distal tip. In partial or half-loading, about one half of the length of the filter device is loaded into the distal tip, while the remainder, typically the filtering element, is left extending from the tip. Particular embodiments of the distal tip incorporate profiled cavities having positive stop features for facilitating half-loading of the filter. A filter device which is half-loaded into the delivery sheath requires only about one half of the relative motion between the sheath and the guide wire for deployment that would otherwise be required by fully loading the filter within the delivery sheath. Thus, half-loading the filter device is advantageous in that it allows for quick filter deployment with minimal manipulation needed for deployment, as well as minimal force.

The present invention reduces the likelihood of emboli formation during the delivery of an intravascular filter by providing a delivery sheath with a radiopaque, low profile, distal tip which minimizes the possibility of abrasion and shearing of the lesion as the sheath crosses a tight lesion. Thus, the delivery sheath of the present invention increases the safety and efficacy of interventional procedures. Other features and advantages of the invention will become more apparent from the following detailed description of the invention, when taken in conjunction with the accompanying exemplary drawings.

DETAILED DESCRIPTION OF THE PREFERRED EMBODIMENTS

The delivery sheath of the present invention may be used with any self-expanding or non-self-expanding deployable intravascular filter. Most self-expanding and non-self-expanding basket type filters are suitable.

Figure 1:
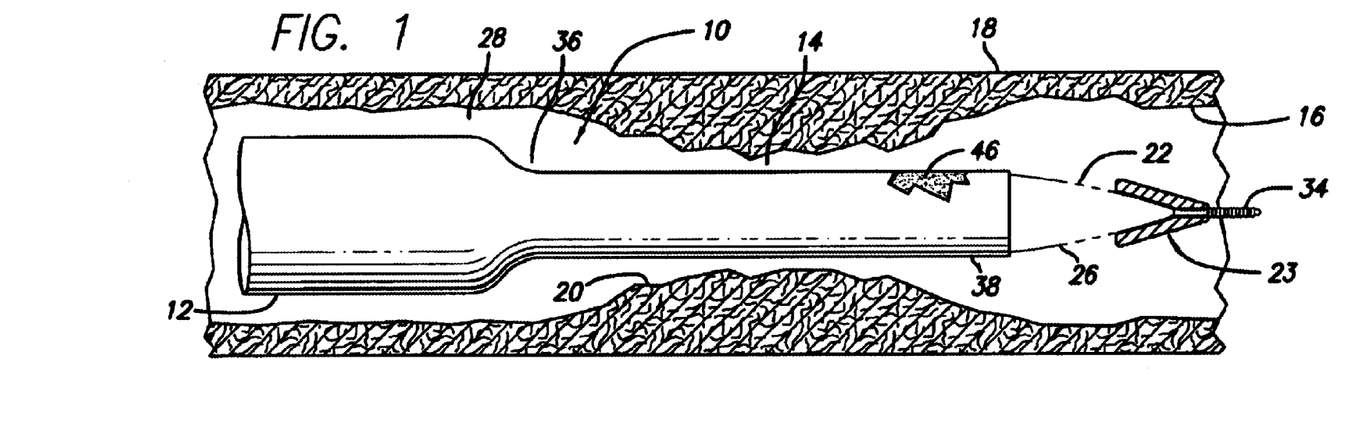
FIG. 1 is a side view of a delivery sheath, embodying features of the present invention, shown positioned within a vessel lumen and extending across an arterial lesion while holding a deployable filter in the half-load position.
Figure 2:
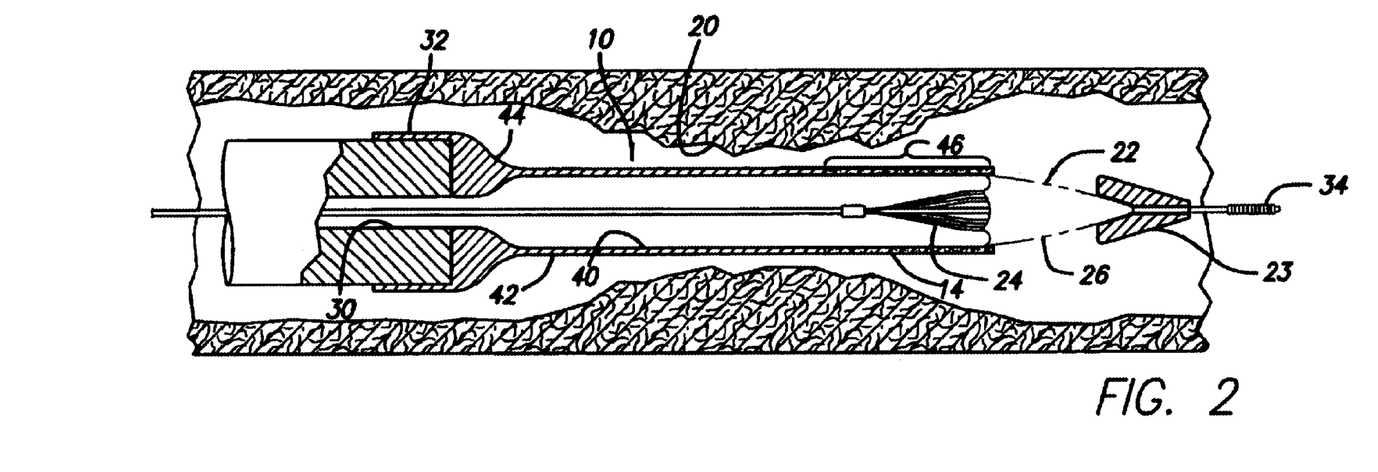
FIG. 2 is a sectional view of the delivery sheath shown in FIG. 1.

With reference to FIGS. 1 and 2, a preferred embodiment of the low profile delivery sheath 10, having a tubular proximal portion 12 and a tubular distal tip 14, is shown in its operating environment within a lumen 16 of an arterial vessel 18. The delivery sheath is shown advanced across a lesion 20 with a deployable filter 22, having a expandable strut assembly 24 and a filtering element 26, held in a partial or half-load position. The filter device 22 is in its reduced diameter state within the distal tip 14 of the sheath 10, ready to be deployed past the lesion for capturing embolic material released into the blood stream. An obturator 23 could be positioned over the tip of the guide wire 34 providing a smooth, atraumatic transition from the guide wire tip to the proximal portion of the filter device system. Although not shown in the other embodiments, a similar obturator could likewise be incorporated into these other designs.

The proximal portion 12, of the delivery sheath 10, includes a proximal end (not shown) and a distal end. A relatively small inner lumen 30 extends from the proximal end to the distal end 28. This proximal portion has a relatively thick tubular wall 32. The inner lumen in the proximal portion of the delivery sheath, needs to be only large enough to allow for the passage of a guide wire 34. The small inner lumen and the tubular wall cooperate to provide the proximal section a high cross sectional stiffness which provides for good pushability within a guiding catheter (not shown) or the vessel lumen 16. The proximal portion may be made of any suitable bio-compatible polymer possessing a relatively high modulus of elasticity ("G"), such as high density polyethylene. Other materials such as high density polypropylene and PeBax 720 are also suitable. The proximal portion may be formed as a continuous length of tubing by any known extrusion, drawing, molding, or similar production process.

The distal tip 14 of the delivery sheath 10 includes proximal and distal ends, 36 and 38 respectively, and has a relatively large inner lumen 40 with a relatively thin wall 42. The proximal end of the distal tip includes a necked down section 44, which reduces the diameter of the distal tip so that the tip may more easily pass across tight arterial lesions and thereby deliver the intravascular filter device 22 to a location distal of the lesion. The necked down region of the distal tip also improves device trackability through tortuous anatomy. The inner lumen is adapted to slidably receive the intravascular filter device in its collapsed state. In the particular embodiment shown in FIG. 2, the filter device may be fully withdrawn into the lumen (full-load position) or the filter may be partially withdrawn into the lumen (half-load position) so that the expandable strut assembly 24 of the filter device, as shown in FIGS. 1 and 2, is collapsed within the lumen while the filtering membrane 26 remains extended distally outward from the distal end of the lumen.

Figure 3:
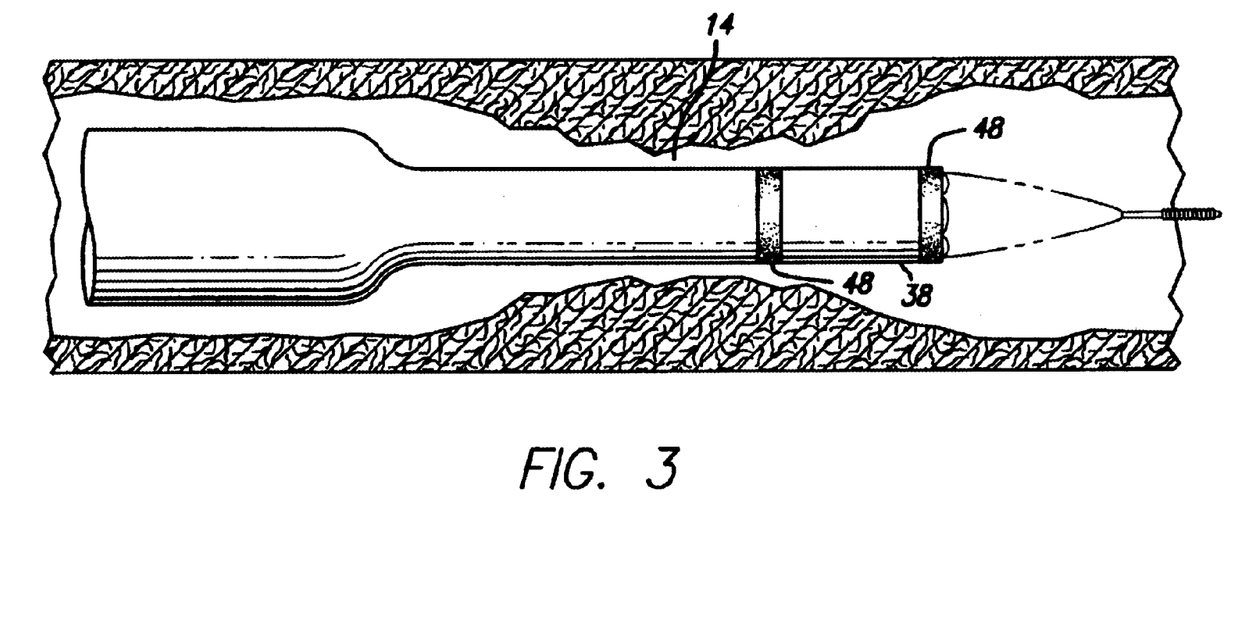
FIG. 3 is another embodiment of the delivery sheath shown in FIG. 1, where the sheath is equipped with radiopaque markers.

It may be desirable to make the distal tip 14 of the sheath 10 radiopaque in order to enable a vascular surgeon to properly visualize and precisely place the distal tip and the filter device 22 in a vessel lumen using fluroscopy or other x-ray visualization procedures. In the embodiment shown in FIGS. 1 and 2, the distal tip is entirely radiopaque. This is achieved by molding the distal tip from a polymer containing radiopaque particles 46 held in suspension within the polymer. Bismuth particles are particularly well suited to this application, however other radiopaque materials which may be procured in particle form such as platinum, gold, silver, barium oxide, and tantalum, are also suitable. Alternatively, the distal end 38 of the distal tip may be equipped with a plurality of discrete radiopaque markers 48 at fixed locations along the tip, as shown in FIG. 3.

Figure 4:
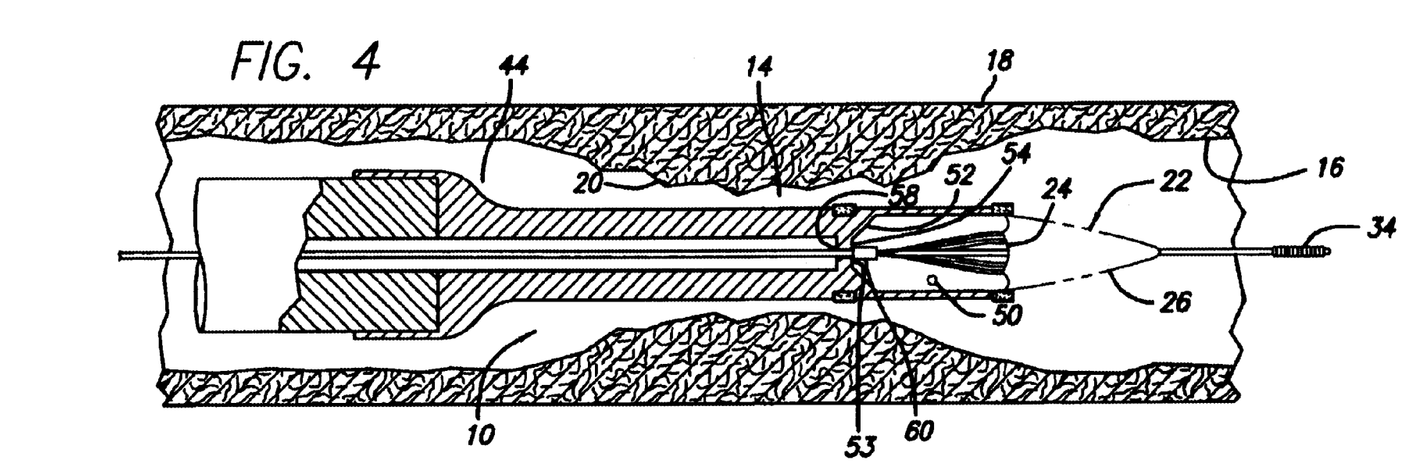
FIG. 4 is a sectional view of a delivery sheath made in accordance with the present invention showing a profiled cavity with beveled faces for holding a deployable filter.
Figure 5:
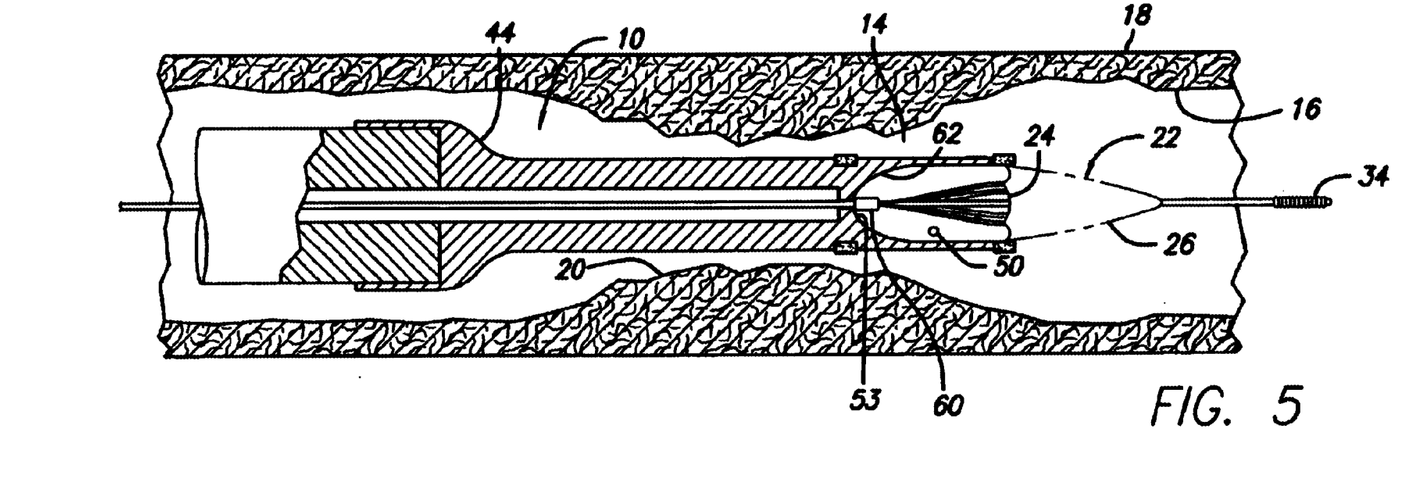
FIG. 5 is a sectional view of another delivery sheath made in accordance with the present invention showing a profiled cavity of parabolic shape for holding a deployable filter.

Referring now to FIGS. 4 and 5, two additional embodiments of the distal tip 14 are shown. These embodiments are particularly useful for deploying embolic filters in the half-load configuration. FIG. 4 depicts an embodiment where the distal tip includes a cylindrical cavity 50 terminating in a chamfered or conical surface 52, which aids in loading the filter device 22. This embodiment also includes a bearing surface 54 which contains a through-hole 58 for the guide wire 34. The hole is sized to be a loose slip fit with the guide wire. A positive stop 53 for loading the filter may be formed by attaching a radiopaque marker 60 to the guide wire just proximal of the intravascular filter. The radiopaque marker functions as a positive stop by abutting the bearing surface when the intravascular filter is loaded into the delivery sheath by pulling on the guide wire. FIG. 5 depicts an additional embodiment of the distal tip which includes the cylindrical cavity and a parabolic end surface 62. The parabolic end surface may provide easier loading with certain filter configurations.

The distal tip 14 may be formed from any bio-compatible polymer material possessing a low modulus of elasticity (G).

Examples of suitable materials are low density polyethylene, low density polypropylene, and PeBax 40b, as well as the polyolefinic ionomers of the sodium, lithium and zinc types. These ionomers are commercially available from the E. I. Dupont de Nemours Corporation under the trademark SURLYN. Polyolefinic ionomers which have been irradiated to cross link the polymers are also suitable as are blends of polyolefin and polyethylene. Other bio-compatible polymeric materials may also be suitable. The distal tip 14 may be formed by any known extrusion, injection molding technique, or similar production technique.

The distal tip 14 may be co-molded with the proximal portion 12 to form a single unitary delivery sheath 10, as is shown in FIGS. 1–3. Co-molding techniques are known in the art. Alternatively, the distal tip 14 may be formed as a separate component, as is shown in FIGS. 4 and 5. When formed as a separate component, the distal tip may be attached to the proximal portion of the sheath by adhesives, ultrasonic welding, heat shrinking using shrinkable tubing or other suitable methods. After fabrication, selected lengths of the delivery sheath may be packaged in sealed inert polyethylene bags and then sterilized by irradiation techniques well known to those skilled in the art. In a typical interventional procedure, coronary or carotid application the overall length of the sheath is about 135 cm, with the relatively stiff proximal portion being about 130 cm long and the distal tip being about 10 cm long.

Referring now to FIG. 4, a preferred method of use of the delivery sheath 10 of the present invention is as follows. A guiding catheter (not shown) is percutaneously introduced into a patient's vasculature, using a conventional Seldinger technique, and is advanced through the patient's body lumen 16 until its distal end lies proximal to and somewhat removed from the arterial lesion 20. Preferably, the guiding catheter is equipped with a radiopaque marker on its distal end. A vascular surgeon may accurately place the guiding catheter within body lumen by tracking the progress of radiopaque marker with x-ray or similar visualization apparatus.

Once the guiding catheter has been placed, the delivery sheath 10 is back-loaded with the guide wire 34 and the filter device 22. Back-loading is accomplished by threading the proximal end of the guide wire through the distal end 38 of the delivery sheath. Attached to the distal end of the guide wire is the intravascular filter device. Once the guide wire is threaded through the delivery sheath, the filter device may be gently compressed and loaded into the distal tip 14 of the delivery sheath by gently pulling on the proximal end of the guide wire which should be extending from the proximal end of the delivery sheath. Alternatively, a commercial available funnel introducer may be used to reduce the diameter of the filter device before loading the filter device int the delivery sheath. This technique reduces the force necessary to load the filter device into the delivery sheath. After a small amount of force is applied to the guide wire, the radiopaque marker 60 attached to the guide wire will abut the bearing surface 54 of the cylindrical cavity 50. At this point the filter is in the half-load position and is ready for deployment. Alternatively, one of the distal tip embodiments depicted in FIGS. 1–3 may be employed. In this case, the filter device may be fully withdrawn into the distal tip, or the filter device may partially extend from the distal tip at the vascular surgeons discretion.

The back-loaded delivery sheath 10 is subsequently advanced through the proximal end of the guiding catheter and out of the distal end until the sheath has crossed the arterial lesion 20. Exact placement of the distal tip 14 and consequently the filter device 22 may be easily determined by tracking the progress of the bismuth or barium oxide loaded radiopaque distal tip (preferred), or alternatively the radiopaque marker equipped distal tip, with fluroscopy apparatus. Once in position, deployment may be achieved by pulling backward on the delivery sheath while holding the guide wire in place. An alternative deployment method is to push forward on guide wire while holding the delivery sheath in place. Upon deployment of the filter device, the delivery sheath is withdrawn and an apparatus for an angioplasty or other interventional procedure may advance through the guiding catheter and over the guide wire core.

It will be appreciated that a new delivery sheath which minimizes the device crossing profile along with formation of embolic particles during the delivery of an intravascular filter has been presented. While only the presently preferred embodiments have been described in detail, as will be apparent to those skilled in the art, modifications and improvements may be made to the device disclosed herein without departing from the scope of the invention. Accordingly, it is not intended that the invention be limited, except as by the appended claims.

What is claimed is:

1. A sheath for delivering and deploying an intravascular filter device within a body lumen, comprising:
   an elongated, tubular proximal portion adapted for deployment within a body lumen and a tubular distal tip extending from the proximal portion, wherein the outside diameter of the distal tip is less than the outside diameter of the proximal portion; and
   the distal tip has a cavity sized for slidable receipt of an intravascular filter device.
2. The delivery sheath of claim 1, wherein:
   the distal tip includes means for achieving radiopacity.
3. The delivery sheath of claim 1, wherein:
   the means for achieving radiopacity comprises a plurality of radiopaque marker bands attached to the distal tip.
4. The delivery sheath of claim 2, wherein:
   the means for achieving radiopacity comprises radiopaque particles in suspension within a polymer which forms the tip.
5. The delivery sheath of claim 4, wherein:
   the radiopaque particles are bismuth particles.
6. The delivery sheath of claim 4, wherein:
   the polymer is polyethylene.
7. The delivery sheath of claim 4, wherein:
   the polymer is PeBax 40D.
8. The delivery of sheath of claim 1, wherein:
   the distal tip is sufficiently long to fully enclose the intravascular filter.
9. The delivery sheath of claim 1, wherein:
   distal portion is formed from a polymer material with a modulus of elasticity lower than that of the material which forms the proximal portion.
10. The delivery sheath of claim 9, wherein:
    the proximal portion is formed from high density polyethylene and the distal is formed from low density polyethylene.
11. The delivery of sheath of claim 1, wherein:
    the proximal portion and the distal tip are co-molded to form a single unitary sheath.
12. The delivery sheath of claim 1, wherein:
    the proximal portion and the distal tip are formed as discrete components and are joined to form a unitary sheath.
13. The delivery sheath of claim 1, wherein:
    the proximal portion has a thick wall with a relatively small lumen sized for receipt of a guidewire and wherein the distal portion has a comparatively thin wall and a comparatively large lumen for receipt of a filter device.
14. A sheath for delivering and deploying an intravascular filter within a body lumen, the sheath comprising:
    an elongated proximal portion having proximal and distal ends and a lumen extending therebetween, the proximal portion being adapted for deployment in a body lumen; and
    a distal tip connected to the proximal portion, wherein the outside diameter of the distal tip is less than the outside diameter of the proximal portion, the distal tip including a profiled cavity having a through-hole for communicating with the lumen of the proximal portion, wherein the profiled cavity is adapted to slidably receive and hold an intravascular filter in a half-load position.
15. The delivery sheath of claim 14, wherein:
    the profiled cavity is cylindrical with a conical end portion.
16. The delivery sheath of claim 14, wherein:
    the profiled cavity is cylindrical with a parabolic end portion.
17. The delivery of sheath claim 14, wherein:
    the proximal portion and the distal tip are co-molded to form a single unitary sheath.
18. The delivery sheath of claim 14, wherein:
    the distal tip includes means for achieving radiopacity.
19. The delivery sheath of claim 18, wherein:
    the means for achieving radiopacity comprises a plurality of radiopaque marker bands attached to the distal tip.
20. The delivery sheath of claim 18, wherein:
    the means for achieving radiopacity comprises radiopaque particles in suspension within a polymer which forms the tip.
21. The delivery sheath of claim 20, wherein:
    the radiopaque particles are bismuth particles.
22. The delivery sheath of claim 20, wherein:
    the radiopaque particles are barium oxide particles.
23. A delivery system for delivering an intravascular filter device within a body lumen, the system comprising:
    an expandable filter device deployable within a vessel lumen;
    a guide wire having proximal and distal ends, wherein the filter device is attached to the distal end of the guide wire;
    a delivery sheath having an elongated tubular proximal portion and a tubular distal tip connected to the proximal portion, wherein the outside diameter of the distal tip is less than the outside diameter of the proximal portion and the proximal portion and distal tip are adapted for deployment within a body lumen;
    the distal tip including a cavity having a hole for communication with the lumen of the proximal portion, the cavity being adapted for slidable receipt of an intravascular filter;
    the distal tip further including radiopaque means for achieving radiopacity, wherein the tip is visible during fluoroscopy;
    means for positively locating the filter within the profiled cavity; and the proximal end of the guide wire being threaded through the distal tip of the delivery sheath, wherein the filter is seated within the profiled cavity.

24. The delivery system of claim 23, wherein:

the radiopaque means comprises barium particles held in suspension within the polymer which forms the tip.

25. The delivery system of claim 24, wherein:

the radiopaque means comprises a plurality of radiopaque markers attached to the tip.

26. The delivery system of claim 23, wherein:

the means for positively locating the filter within the profiled cavity includes a radiopaque marker affixed to the guide wire proximal of the filter and a bearing surface withing the profiled cavity, wherein the radiopaque marker abuts the bearing surface when the guide wire is fully threaded through the delivery sheath.

27. The delivery system of claim 23, wherein:

the profiled cavity is adapted to slidably receive and hold an intravascular filter in a half-load position.

28. The delivery system of claim 23, further including:

an obturator which provides a smooth transition from the tip to the filter device.

* * * * *

UNITED STATES PATENT AND TRADEMARK OFFICE
CERTIFICATE OF CORRECTION

PATENT NO. : 6,679,902 B1
DATED : January 20, 2004
INVENTOR(S) : William J. Boyle et al.

It is certified that error appears in the above-identified patent and that said Letters Patent is hereby corrected as shown below:

Column 3,
Line 61, delete "deployement" and insert -- deployment --.

Column 6,
Line 53, delete "int" and insert -- into --.

Column 7,
Line 59, after "distal" insert -- tip --.

Column 10,
Line 2, delete "withing" and insert -- within --.

Signed and Sealed this

Thirteenth Day of July, 2004

JON W. DUDAS
*Acting Director of the United States Patent and Trademark Office*